United States Patent [19]

Ramachandran

[11] Patent Number: 4,720,374
[45] Date of Patent: Jan. 19, 1988

[54] CONTAINER HAVING A SONICATION COMPARTMENT

[75] Inventor: Narayanaswamy Ramachandran, Newark, Del.

[73] Assignee: E. I. Du Pont de Nemours and Company, Wilmington, Del.

[21] Appl. No.: 757,576

[22] Filed: Jul. 22, 1985

[51] Int. Cl.[4] .............................................. G01N 1/10
[52] U.S. Cl. .................................... 422/310; 206/538; 422/102; 422/261; 422/128
[58] Field of Search .................... 422/58, 61, 65, 102, 422/261, 266, 310, 128; 206/0.5, 524.7, 538, 539, 569; 220/213, 229, 359; 356/244, 246; 435/805

[56] References Cited

U.S. PATENT DOCUMENTS

| D. 266,589 | 10/1982 | Gilford et al. ........................ D24/31 |
| 3,190,731 | 6/1965 | Weiskopf ............................. 422/102 |
| 3,477,821 | 11/1969 | Hamilton ............................... 422/61 |
| 3,477,822 | 11/1969 | Hamilton ............................... 422/61 |
| 3,480,398 | 11/1969 | Hamilton ........................... 422/61 X |
| 3,480,399 | 11/1969 | Hamilton ........................... 422/61 X |
| 3,545,934 | 12/1970 | Dryden et al. ........................ 422/61 |
| 3,545,935 | 12/1970 | Kearns ................................... 422/61 |
| 3,554,705 | 1/1971 | Johnston et al. ...................... 422/61 |
| 3,582,283 | 6/1971 | Mirasol, Jr. ........................... 23/253 |
| 3,582,285 | 6/1971 | Hamilton ............................... 23/259 |
| 3,691,017 | 9/1972 | Brown et al. ..................... 195/103.5 |
| 3,788,815 | 1/1974 | Rohrbaugh .......................... 422/102 |
| 3,994,594 | 11/1976 | Sandrock et al. ................... 356/246 |
| 4,053,284 | 10/1977 | Posch .................................. 436/807 |
| 4,083,638 | 4/1978 | Sandrock et al. ................... 356/246 |
| 4,111,304 | 9/1978 | Lucas .............................. 206/538 X |
| 4,251,159 | 2/1981 | White .................................. 356/246 |
| 4,303,616 | 12/1981 | Kano et al. .......................... 422/102 |
| 4,357,301 | 11/1982 | Cassaday et al. ...................... 432/64 |
| 4,466,740 | 8/1984 | Kano et al. .......................... 356/246 |
| 4,528,159 | 7/1985 | Liston .............................. 422/64 X |

Primary Examiner—Barry S. Richman
Assistant Examiner—William R. Johnson

[57] ABSTRACT

A container for the dissolution of a tablet of material is characterized by a plurality of projections mounted within the container. The projections cooperate to define a tablet-receiving recess adapted to confine a tablet inwardly therewithin in a relatively high energy zone during sonication of the tablet. Gaps between the projections define recirculating liquid channels whereby hydrating liquid passing through the tablet-receiving recess may be recirculated to other regions of the compartment.

2 Claims, 9 Drawing Figures

CONTAINER HAVING A SONICATION COMPARTMENT

CROSS-REFERENCE TO RELATED APPLICATIONS

Subject matter disclosed herein is disclosed or claimed in the following copending applications filed contemporaneously herewith:

Method and Apparatus for Ultrasonic Interface Detection, filed July 22, 1985 and accorded Ser. No. 757,572; now abandoned;

Self-Cleaning Ultrasonic Horn, filed July 22, 1985 and accorded Ser. No. 757,574; and Resealable Lid Structure For A Container, filed July 22, 1985, and accorded Ser. No. 757,575.

BACKGROUND OF THE INVENTION

1. Field of the Invention

The present invention relates to a container configured to facilitate the dissolution or dispersion of tableted or partially emulsified material using ultrasonic energy.

2. Description of the Prior Art

Techniques are known in the art whereby ultrasonic energy is utilized to dissolve tableted material. Exemplary of such prior knowledge is U.S. Pat. No. 3,582,285 (Hamilton) which discloses a package for tableted chemicals. Ultrasonic energy is applied from the exterior of the package and coupled into a reaction compartment such that a tablet of material disposed within the compartment is dissolved. The patent's disclosure recognizes that the application of ultrasonic energy results in the creation of relatively high sonic energy zones within the compartment. However, experience has shown that a tableted material tends to migrate and the fragments produced by sonic dissolution tend to disperse within the compartment from the high energy zone to zones of relatively less energy. As a result relatively long periods of exposure to ultrasonic energy may be required to completely dissolve the material of the tablet.

Such prolonged sonication may result in excess heating of the body of liquid in which the tablet is disposed. This excessive heating may be especially deleterious when the tableted material is being dissolved within a body of liquid (e.g., a sample and/or reagent) that is used for the analysis of biological liquids. Accordingly, it would be advantageous to provide a container arrangement whereby tableted or partially emulsified material may be dissolved or dispersed expeditiously (i.e., in less than one minute) by the application of ultrasonic energy from a point in the interior of the container. Further, it is believed advantageous to provide a container which exhibits a structure which confines the tableted material to a relatively high energy zone thereby preventing the migration of the material, tablet or portions of the tablet from this zone, thus decreasing the dissolution time.

When storing a liquid reagent and/or specimen care must be exercised to minimize evaporation. Simultaneously, however, whatever structure is used to inhibit evaporation must be compatible with the requirements of access to the liquid during use. Accordingly it is believed advantageous to provide a lid structure which is resealable to permit extended storage without evaporation and, simultaneously to accommodate mixing or sampling probes. Lid structures which realize these goals are available in the art. Exemplary of such devices is that disclosed in U.S. Pat. No. 3,994,594 (Sandrock et al.). However, such lid structures are believed incompatible for use in an environment in which the mixing and/or sampling probe is other than a sharp implement. Moreover, in multi-compartmented containers it is believed desirable to provide a lid structure which minimizes vapor transmission from compartment to compartment, thus minimizing contamination of the contents of one compartment by the contents of another compartment.

The source of sonic energy used for dissolving tableted material is a device known as an ultrasonic horn. The horn is a relatively elongated member which vibrates at an ultrasonic frequency as a result of a conversion of an electrical excitation signal into a mechanical vibration. Ultrasonic horns may be provided with a bore through which a liquid may be flowed through the horn and out of the tip. This structure allows injection of one liquid into another, as in emulsion formulation, misting or fogging. Such ultrasonic horns are produced by, among others, Heat Systems - Ultrasonics Inc., Farmingdale, N.Y. Other horn structures are known which operate as atomizers by pumping a liquid from a reservoir by the pumping action generated as a result of an asymmetric sound field forming bubbles in the bore. Exemplary of this type of device is that shown in the Article by Lierke, "Ultrasonic Atomizer Incorporating A Self-Acting Liquid Supply", 5 Ultrasonics, 214 (1967).

However, when using a flow-through horn in a biological testing environment care must be taken to prevent "carry-over", i.e., contamination of a subsequent liquid with particulate matter deposited within the horn by a preceding liquid. It would therefore be advantageous to provide an ultrasonic horn assembly having a self-cleaning capability such that the carry-over of particulate matter is minimized or eliminated.

SUMMARY OF THE INVENTION

The present invention relates to a container having a hydration compartment defined therein. The container may receive a hydrating liquid and one or more tablets of solid material to be dissolved or dispersed therein. The container has an array of sonication-improving projections mounted therein which cooperate to define a tablet-receiving recess. The projections are spaced from each other to provide recirculating channels which communicate with both the tablet-receiving recess and the remainder of the volume of the container such that, in use, the projections act to confine a tableted material within a relatively high ultrasonic energy zone and simultaneously permit a flow of hydrating liquid from the high energy zone through the channels thereby to rapidly effect the dissolution of the tableted material.

BRIEF DESCRIPTION OF THE DRAWINGS

The invention may be more fully understood from the following detailed description thereof taken in connection with the accompanying drawings which form a part of this application and in which.

DETAILED DESCRIPTION OF THE INVENTION

Throughout the following detailed description similar reference numbers refer to similar elements in all figures of the drawings.

Figure 1:
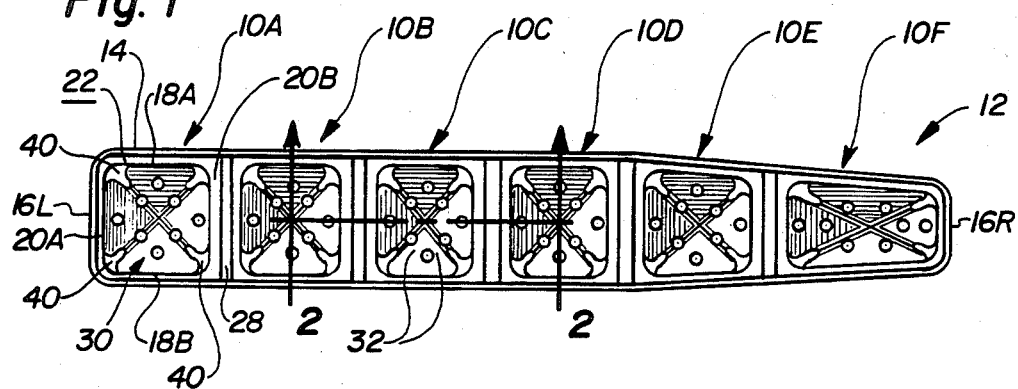
FIG. 1 is a plan view of multi-container strip useful for carrying a liquid for biological testing in which each container has a compartment with a tablet-receiving recess defined by a plurality of projections formed therewithin.

Referring to FIG. 1 shown is a plurality of hydration containers 10A through 10F conveniently arranged in an end-to-end relationship to form a container strip generally indicated by the reference character 12. As will be developed more fully herein each of the containers 10A through 10F is provided with an array of the preferred form of sonication-improving projections generally indicated by reference character 30 provided in accordance with the present invention.

The container strip 12 may be fabricated in any convenient manner. In the embodiment shown in FIG. 1 the container strip 12 includes a rigid peripheral band 14 formed of a suitable material, such as an inert plastic. The band 14 is either joined to or formed integrally with each of the containers 10 such that, in the preferred case, the container strip 12 generally tapers in a substantially elongated wedge-like manner from a first edge 16L toward a second edge 16R. This wedge-shaped plan profile for the container strip 12 facilitates the mounting of a plurality of such strips in a circumferentially adjacent, generally radially extending relationship across a rotatable reagent carrying plate such as that disclosed in the analysis instrument disclosed and claimed in copending application titled Analysis Instrument Having Heat-Formed Analysis Cuvettes, Ser. No. 642,814, filed Aug. 21, 1984 and assigned to the assignee of the present invention. It should, however, be appreciated that the individual containers 10 may take any predetermined configuration and the containers 10 may be used alone or arranged together in any convenient number and in any convenient manner and remain within the contemplation of this invention.

Figure 2:
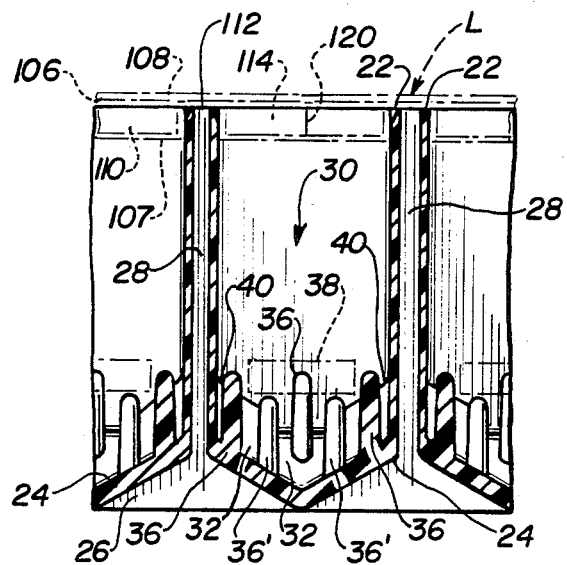
FIG. 2 is a side elevational view taken along section lines 2—2 of FIG. 1.

Each of the containers 10, whether arranged singularly or in a container strip 12, in the embodiment shown, is formed of a suitable inert plastic material and includes a compartment defined by generally opposed pairs of generally parallel and integrally formed sidewalls 18A, 18B and end walls 20A, 20B. The upper surfaces of the sidewalls 18A and 18B and endwalls 20A and 20B (together with the upper surface of the band 14 in the vicinity thereof) register to define a substantially planar sealing surface 22 peripherally surrounding the open upper end of the container 10. The compartment of the container 10 is closed by a downwardly sloping inverted pyramidal floor 24 (FIG. 2). In the embodiment shown in FIG. 1 the sidewalls 18A, 18B of each container 10 are joined to the peripheral band 14. Further, the endwall 20A of the container 10A and the endwall 20B of the container 10F are likewise connected to the band 14. The band 14 extends slightly below the lower ends of the containers 10 and thus define a support strut 26 whereby the container strip 12 may be set on a suitable work surface. It the container 10 were used singly any convenient arrangement may be used to support the container on a work surface. As seen in FIG. 1 the containers 10A, 10B, 10C and 10D are arranged in a substantially square configuration while the containers 10E and 10F are configured in a more rectangular configuration. However, it is to be understood that individual containers may be defined to be other than rectangular or square in plan and be provided with other than a downwardly sloping floor 24 and yet remain within the contemplation of the present invention.

Adjacent endwalls 20A, 20B of adjacent containers 10 (e.g., the containers 10B, 10C and 10D, FIG. 2) are spaced from each other by a predetermined gap 28 to enhance the thermal and vapor isolation of each of the containers 10. In accordance with the preferred embodiment of the invention the container strip 12 is formed by injection molding from a polyallomer material. Of course, other manufacturing techniques and materials of construction may be utilized and remain within the contemplation of the present invention.

As noted earlier, in accordance with the present invention each of the containers 10 carries an array of mutually spaced sonication improving projections 30. The individual projections 30 are spaced from each other to define channels 32 therebetween. With reference to FIGS. 1 and 2 the preferred embodiment of the projections 30 is shown. In this embodiment the projections 30 take the form of a set of substantially finger-like members 36, 36' extending vertically upwardly in axially parallel relationship from the floor 24 of each container 10. Selected ones 36 of the finger-like members project upwardly from the floor 24 for a distance greater than the others 36' of the members of the set. Such a relationship thereby defines a tablet-receiving recess 38 disposed generally centrally within the container 10. The spaces between the finger-like members 36, 36' define channels 32 which, as will be explained herein, permit hydrating liquid flow into and through the recess 38. It should be appreciated that the sonication improving projections 30 may be disposed in any convenient orientation or at any convenient location within the container 10. For example, if the finger-like members 36, 36' are used to define the projections 30, such members may be inclined with respect to the vertical axis of the container 10 and may be mounted to the sidewalls 18A, 18B and/or the endwalls 20A, 20B in addition to or in place of their mounting on the floor 24. As also seen from FIGS. 1 and 2 generally planar members 40 extend diagonally outwardly from the corners of the container 10 to assist in guiding of the circulating hydrating liquid. As seen the side surfaces of the planar members 40 lie substantially perpendicularly to the floor 24.

Figure 3A:
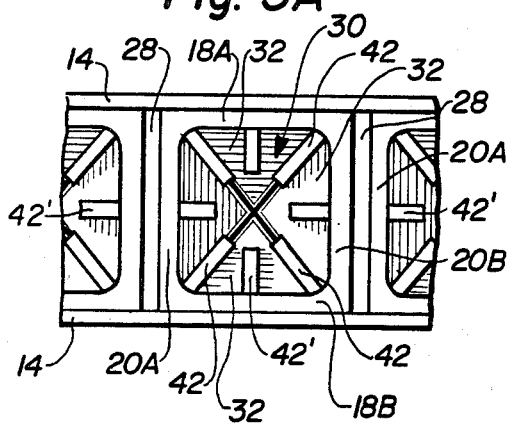
FIG. 3A through 3D are each plan views of an individual container illustrating alternate embodiments of the tablet-receiving recess defined by projections in accordance with the present invention.

Other embodiments of the sonication improving projections 30 are shown in FIGS. 3A through 3D. These figures depict plan views of individual containers 10 and illustrate the form and arrangement with vertical side surfaces of alternate embodiments of the sonication improving projections. In FIG. 3A the projections 30 are in the form of plate-like members 42 generally similar to the members 40 shown in FIGS. 1 and 2. Some of the plates 42 extend inwardly from the corners of the container 10 while others 42' extend inwardly from the container from the sidewalls 18 and endwalls 20 thereof.

The plates 42, 42' are thus respectively oriented substantially along diagonals and transverses of the container 10. The inner ends of the plates 42, 42' preferably, but not necessarily, extend substantially vertically of the container 10 from the floor 24 of the container. The lower edges of the plates 42, 42' may integrate with the floor 24, if desired. The vertically oriented inner ends of the plates 42, 42' cooperate to define on the interior of the container the centrally located tablet-receiving recess 38. The spaces between the plates 42, 42' define the channels 32 through which hydrated liquid may flow in a manner to be described.

Figure 3B:
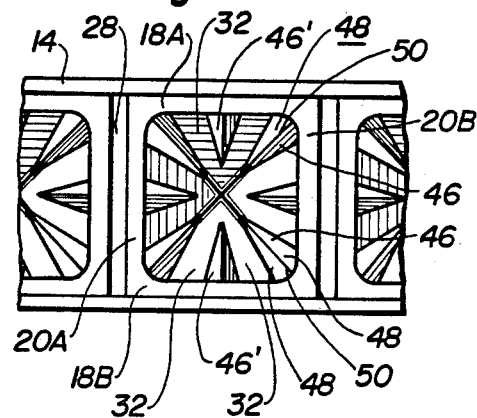

In FIG. 3B the projections 30 are in the form of inwardly directed pyramid structures 46, 46'. The pyramidal structures 46, 46' are each defined by faces 48, which are joined along an apex 50 that substantially align in the respective cases of the structures 46 and 46' with the diagonals and transverses of the container 10. The structures 46, 46' are thus mounted in positions analogous to the plates 42, 42' and are thus substantially diagonally and transversely disposed within the container 10. The spaces between the structures 46, 46' define the channels 32 for the purpose to be described.

Figure 3C:
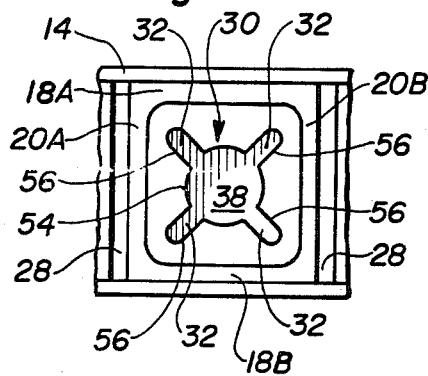
Figure 3D:
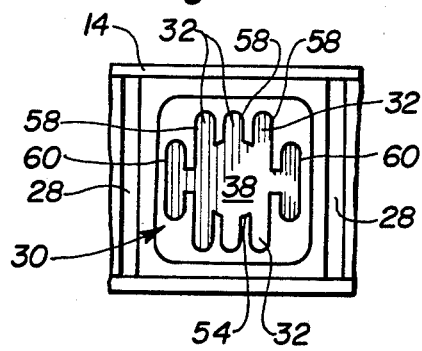

In FIG. 3C the floor 24 of the container 10 is provided with a central circular region 54 which is intersected by diagonal grooves 56 thereby to respectively define the tablet-receiving recess 38 and the channels 32. In this and in FIG. 3D the floor 24 is substantially flat. The projections 30 are thus defined as those portions of the material of the container 10 between the grooves 56. Similarly, in FIG. 3D the central region 54 again defines the recess 38. In this instance the region 54 is interrupted by a plurality of generally parallel grooves 58 which serve to define the channels 32. End grooves 60 are also provided. The projections 32 are defined as those portions of the material between the grooves 58, 60.

In the use of this invention a tableted material to be dissolved or dispersed in introduced into a hydrating liquid introduced within the container. Sonifying energy is provided from an ultrasonic transducer such as the device (discussed in connection with FIG. 6) lowered into the container 10 through the open end thereof. Actuation of the ultrasonic transducer introduces ultrasonic energy and directs the same substantially axially of the container to encompass the tablet-receiving recess 38. The ultrasonic energy may be applied continuously or in bursts, with a relatively constant or varying frequency. The tablet (or plurality of tablets) of material to be dissolved or dispersed into the liquid in the container migrates toward and is confined within tablet receiving recess 38. It is found that the migration of the material to the recess 38 occurs whatever the initial disposition of the material within the container 10. The structural relationship between the projections 30 serves to define a recess 38 which defines a relatively high ultrasonic energy region within the container in which the material to be dissolved is received and confined. Any entrapped air beneath the material to be dissolved and hydrating liquid flow is permitted from other regions on the interior volume of the container through the high energy sonication region and then outwardly through the channels 32 between the projections 30. It is believed that if the embodiment of the projections 30 shown in FIGS. 1 and 2, i.e., the finger-like members, is used reflection of ultrasonic energy from the walls and floor of the container into the recess 38. As a result of the confinement of the material to the high energy zone relatively high speed dissolution of the material due to the application of ultrasonic energy may be effected. Times of dissolution of the material of less than one minute are possible. Concomitantly heating effects which may deleteriously affect the hydrating liquid and/or the chemical release by dissolution are thereby avoided.

In view of the foregoing those skilled in the art may readily appreciate that the provision of any suitable projections disposed either on the floor and/or from the walls of the container which serve to define both a tablet-receiving recess and recirculating gaps to permit the circulation of hydrating liquid through the high energy zone act in use to enhance the application of ultrasonic energy to efficiently and expeditiously dissolve the tablet material. Any such structural combination which forms the relatively high energy tablet-receiving recess and defines a relatively high ultrasonic energy zone coupled with and communicating recirculating channels lies within the contemplation of the present invention.

Figure 6:
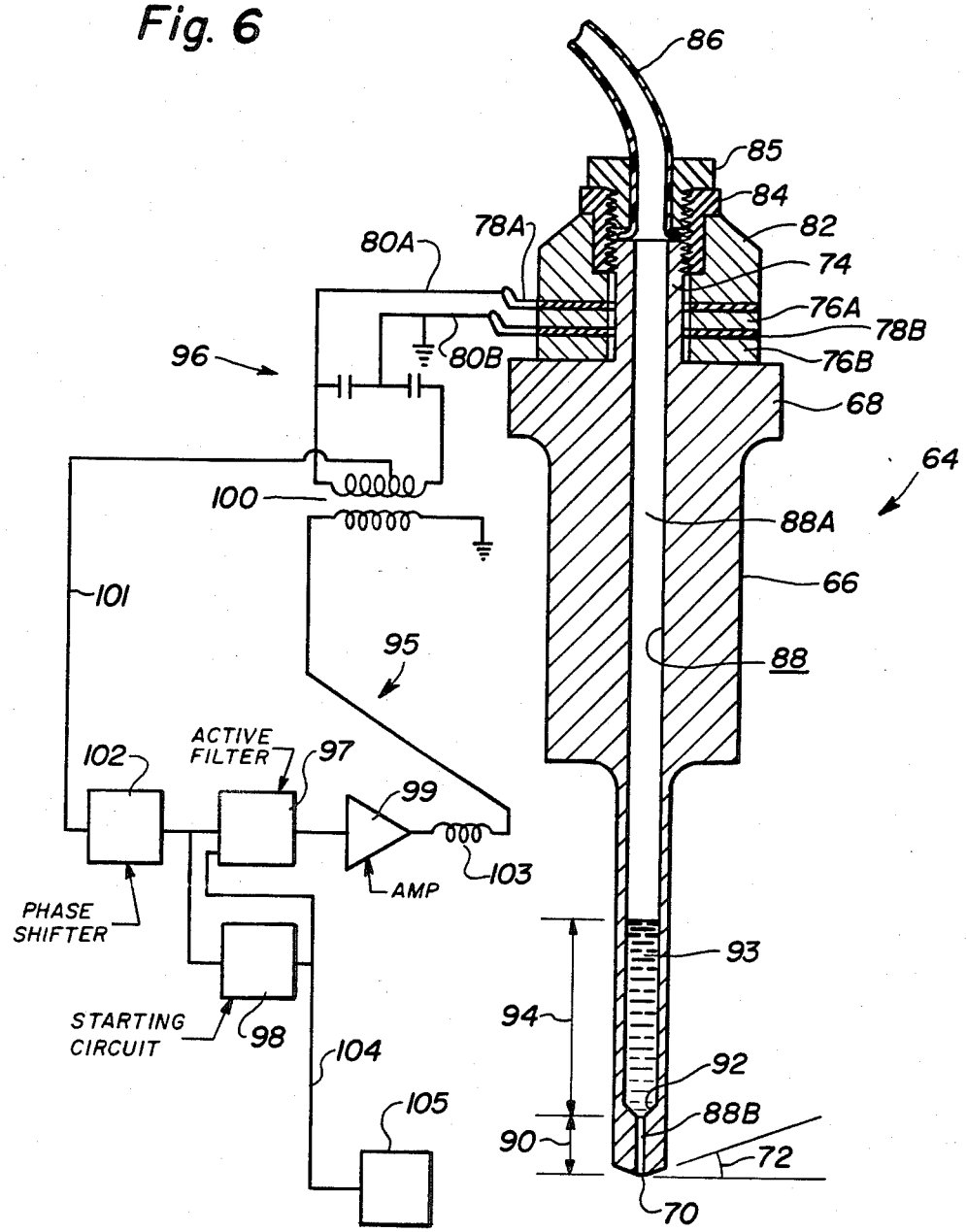
FIG. 6 is a side sectional view of an ultrasonic horn in accordance with the present invention.

An ultrasonic transducer or probe 64 in accordance with the present invention is shown in FIG. 6. The body or horn portion 66 of the transducer 64 is an elongated axial member extending from an enlarged head portion 68 to a beveled tip 70. The tip 70 defines an angle 72 measured with respect to a reference line perpendicular to the axis of the bore within the range from 0° to 45°, more particularly from 30° to 45°, and precisely 30°. An axially projecting threaded boss 74 extends upwardly from the head 68. A pair of piezoelectric crystals 76A, 76B with associated electrodes 78A, 78B are received about the boss 74. Leads 80A, 80B extend from the electrodes 78A, 78B, respectively.

In the embodiment shown in FIG. 6 the crystals 76 are held in place against the head 68 by a backpiece 82. A nut 84 threads onto the boss 74 and clamps the assembly together. A tubing connector 85 is threadedly received onto the upper portion of the threads of the nut 84. A tube 86 mounted within the connector 84 may thus be quickly and easily interconnected with the ultrasonic transducer 64.

A bore 88 extends centrally and axially through transducer 66 where it communicates with the end of the tube 86. The internal diameters of the tube 86 and the upper portion 88A of the bore 88 are substantially equal. As seen in FIG. 6 the relatively larger diameter portion 88A extends over substantially all of the length of the transducer 66. Disposed within a predetermined distance 90 of the end of the horn 66 is an inwardly tapering beveled shoulder 92. The presence of the shoulder 92 narrows the bore 88 to a lesser diameter portion 88B. In accordance with the invention the shoulder 92 is located within the predetermined close distance 90 from the antinode (or the tip of the beveled end 66) of the vibrating horn 62.

In operation the tube 86 is connected to suitable aspirating and hydrating sources whereby hydrating liquid may be dispensed from and aspirated into the transducer 64. To minimize the possibility of carry-over of matter in the bore 88 the bore 88 is cleaned by the microstreaming and cavitating action produced by the abutment of the shoulder 92 against a continuous column 93 of liquid extending a predetermined distance 94 into the enlarged portion 88A of the bore.

An ultrasonic horn assembly 64 as shown in FIG. 6 is adapted to precisely dispense and aspirate liquid into and from a container 10 and to provide the sonic energy necessary to dissolve a tablet or partially emulsified material. The horn assembly 64 can also be used to mix together at least two liquid materials. Due to the provision of the shoulder 92 the cleaning action generated within the continuous column 94 of liquid is generated which prevents accumulation of matter on the walls of the bore and thus minimizes carryover. It is also believed that the cleaning action extends into liquid within the tube 86, thus minimizing carryover at the interface between the horn and the tube.

The horn assembly 64 may also form a part of an apparatus for detecting the presence of a solid interface (e.g., a lid) or a liquid interface (e.g., the surface of a liquid reagent or a liquid sample.

The leads 80A, 80B are applied to a self resonant power supply network 95 such as that disclosed in U.S. Pat. No. 4,445,064, which patent is incorporated by reference herein. The network 95 includes a motional bridge circuit 96 for generating feedback signals proportional to the vibration of the ultrasonic horn assembly 64 which is modified by means of an active filter 97 in the feedback circuit which is coupled to a starting circuit 98 that raises the Q of the active filter when a signal is not present in the feedback loop to change the active filter from a mode suppressant to a self-oscillating state.

As seen in FIG. 6, the horn assembly 64 is operated in a motional bridge circuit 96 which, in turn, is coupled to the output of constant gain power amplifier 99 via a transformer 100. The motional bridge circuit 96, not only serves to apply excitation power to horn 64, but more importantly, it produces a sinusoidal feedback control voltage on line 101 that (1) corresponds directly with transducer tip frequency, amplitude and phase and (2) remains independent of nonreactive load changes on the transducer. Line 101 connects the motional bridge circuit 96 to the input of the all pass phase shifter circuit 102. Connected to the output of phase shifter 102 is the active filter circuit 97 and the starting circuit 98 to make filter 97 self oscillating. Active filter 97 is connected to the input of power amplifier 99 whose output is connected to transformer 100 through inductance 103 to drive motional bridge circuit 96.

Feedback control voltage of line 101 is the input to phase shifter circuit 102 which is used to tune the phasing of the input sinusoidal signal in such a predetermined amount and direction that the transducer vibrations are constrained to remain in the parallel resonance condition. It is important to note that only the phasing of the feedback signal, and not amplitude, is adjusted so as to not disturb loop gain and the mode suppression function of succeeding active filter circuit 97. Phase shifter circuit 102 is configured as a first-order all pass network with variable phase shift. Its output is a replica (except for phase) of the input AC feedback signal from motional bridge circuit 96.

Active filter 97 is a dual-purpose second-order Q-controlled band pass filter. The primary purpose of filter 97 is to prevent the power supply from driving the transducer system "out of band" into vibrational modes that have not been selected for use. Used in this way, it is called a mode suppressant filter. The secondary purpose of filter 97 does not appear unless the feedback signal on line 101 is lost completely, such as at startup. In this event, starting circuit 98 which monitors the output signal from phase-shifter circuit 102, causes the Q of active filter circuit 97 to increase to the point where filter circuit 97 brakes into oscillation. (Circiut Q is defined as the ratio of resonant frequency ($W_o$) to $-3$ dB bandwidth (BW) or $$Q = W_o/BW$$

The frequency of oscillation is made to be coincident with the preselected natural parallel resonant frequency of the transducer system. The oscillator mode afforded by active filter 97 remains as long as needed to re-establish the feedback control signal on line 101 from motional bridge circuit 96.

A voltage (on the order of seventy volts, RMS) is applied to the horn 64 which is sufficient to just drive the unloaded horn 64 to vibrate at its resonant frequency. The horn operates in the frequency range from 20 to 100 kHz., more particularly 40 to 60 kHz, and specifically at 50 kHz. When the tip 70 of the horn 64 encounters the solid or liquid interface the horn becomes loaded and the horn no longer resonates. The signal in the line 101 is thus lost. As described above and in the incorporated patent the loss of the feedback signal causes the starting circuit 98 to produce a signal on the line 104 to a device 105, e.g., a digital computer. Thus is generated an indication that the horn 64 has encountered an interface.

Each of the containers 10 in the multi-container strip 12 shown in FIG. 1 may be closed by a lid structure L in accordance with the present invention. The lid structure includes a first, lower, support sheet 106 having an array of spaced receptacles 107 therein. Each receptacle 107 occupies a perimetric configuration corresponding to the shape of the open end of the container 10 with which it is associated.

A second, upper, cover sheet 108 overlies the lower sheet 106. The sheet 108 is joined to the sheet 106 along those interfacing portions thereof to thus define a substantially enclosed volume 110 within each receptacle 107. The sheets 106 and 108 are joined by any suitable expedient and define a peripheral flange region 112 entirely surrounding the enclosed volume 110. Disposed within each of the volumes 110 is a thermoplastic elastomer pad 112 such as that sold by West Company of Phoenixville, Pa., under formulation number 8553-3-5-1. The pad 114 is received within each enclosed volume 110 and is sized such that a gap 116 is defined between the walls of the receptacle and the undersurface of the upper sheet 108.

The lid structure L in the above-described assembled relationship is arranged to overlie each container 10 in the strip 12. To facilitate this end the undersurface of the peripheral flange region 112 defined by the jointure of the sheets 106, 108 is heat sealed or otherwise attached to the sealing surface 22 of the compartments 12. In this manner the containers are each closed by an impermeable seal which serves to form an evaporation barrier for the contents of the compartment and to isolate the containers against vapor cross contamination.

Figure 4:
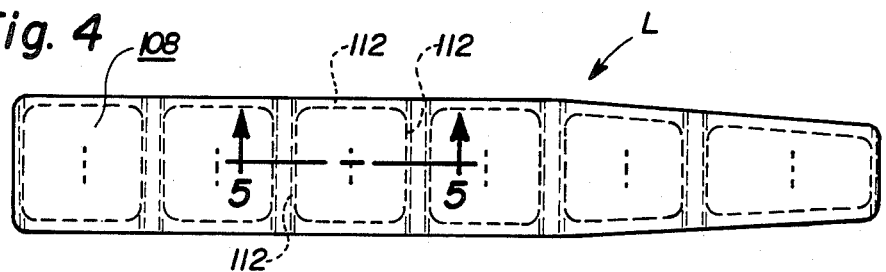
FIG. 4 is a plan view of a resealable lid structure usable with a multi-compartment container of FIG. 1.
Figure 5:
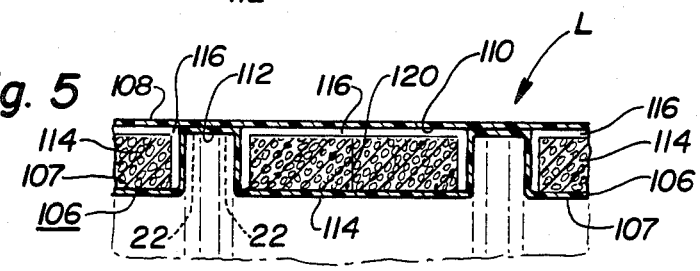
FIG. 5 is a sectional view of the lid structure taken along lines 5—5 of FIG. 4.

Since in the embodiment shown in FIGS. 4 and 5 lower sheet 106 is to be heat sealed to the surface 22 surrounding each container, the material of the sheet 106 abutting the container 10 must be heat sealable thereto. Otherwise any suitable substantially rigid, inert material may be used as the sheet 106. The sheet 108 is, in the preferred embodiment formed of a laminate of (i) an outer polyester film, such as that sold by E. I. du Pont de Nemours and Company under the trademark MYLAR, (ii) a polyvinylidene chloride coating such as that sold by Dow Chemicals Co. under the trademark SARAN, and (iii) an outer barrier sheet of polyethylene. The polyethylene sheet interfaces against the lower sheet and is joined thereto. Of course, any other suitable materials may be used for the sheets 106 and 108. The top sheet 108 forms a vapor barrier to enhance the shelf life of a container covered by the lid L.

The pad 116 may also be implemented using any stretchable, resealable material, such as silicone rubber or natural rubber. In the preferred embodiment the lid is arranged such that the pad 114 projects downwardly into the container. However, the reverse is also possible, i.e., where pad 114 is disposed above the container. If only a single container is being covered the lid may be implemented using a single sheet with a pad secured thereto. Either surface of the sheet may be attached to the container whereby the pad projects into or lies above the container.

The pad 114 may be provided with a slit 120 which defines an entry and exit path whereby an ultrasonic horn, e.g. the horn 64, may be introduced into the container 10. The elastomeric material of the pad 114 is selected so that the pad self-heals as the horn is withdrawn, thereby maintaining a substantially integral evaporation barrier over the container. The pad 114 self-heals even for relative large diameter probes (i.e., on the order of 0.125 inches). Thus the lid structure L is useful in conjunction with relatively blunt probes. Moreover, the material of the pad 114 performs a wiping action on the exterior of the horn as the horn is inserted or withdrawn. This wiping action prevents cross contamination. It has been found that the provision of the gap between the pad and the receptacle facilitates the entry of the probe or horn into the container.

Those skilled in the art having the benefit of the teachings of the present invention as hereinabove set forth may effect numerous modifications thereto. These modifications are, however, to be construed as lying within the scope of the present invention as defined by the appended claims.

What is claimed is:

1. A container having a hydration compartment adapted to receive therein a hydrating liquid and a material to be dissolved or dispersed thereinto, the compartment having sidewalls and endwalls and a floor from which an array of finger-like members project vertically upwardly into the compartment, the fingers being spaced from the sidewalls and endwalls with the tips of predetermined ones of the finger-like members being above the tips of others of the members within the compartment, the members being arranged with respect to each other to define a material receiving recess and being relatively spaced apart to define recirculating gaps therebetween such that, in use, the material to be dissolved by the application of ultrasonic energy from a source introduced into the compartment is confined within a relatively high energy zone defined by the recess and hydrating fluid is recirculated through and out of the relatively high energy zone through the gaps between the finger-like members.

2. The container of claim 1 further comprising planar members having side surfaces extending substantially perpendicularly of the floor, the planar members being oriented substantially on diagonals of the compartment.

* * * * *